(12) United States Patent  (10) Patent No.: US 7,887,766 B2
Klein et al.  (45) Date of Patent: Feb. 15, 2011

(54) WELL PLATE REACTOR

(75) Inventors: David L. Klein, Palo Alto, CA (US);
Stephen G. Boyer, Stockton, CA (US);
Gregory Andronaco, Palo Alto, CA (US)

(73) Assignee: Pall Microreactor Technologies, Inc., Mountain View, CA (US)

( * ) Notice: Subject to any disclaimer, the term of this patent is extended or adjusted under 35 U.S.C. 154(b) by 0 days.

(21) Appl. No.: 12/749,374

(22) Filed: Mar. 29, 2010

(65) Prior Publication Data

US 2010/0184199 A1 Jul. 22, 2010

Related U.S. Application Data

(60) Continuation of application No. 12/024,973, filed on Feb. 1, 2008, now Pat. No. 7,713,486, which is a division of application No. 10/777,581, filed on Feb. 11, 2004, now Pat. No. 7,374,725.

(51) Int. Cl.
*B01L 3/00* (2006.01)

(52) U.S. Cl. .................................................. 422/407

(58) Field of Classification Search ............... 422/102, 422/407
See application file for complete search history.

(56) References Cited

U.S. PATENT DOCUMENTS

| | | | |
|---|---|---|---|
| 797,796 | A | 8/1905 | Delvin |
| 4,618,170 | A | 10/1986 | Fishburne |
| 6,197,575 | B1 * | 3/2001 | Griffith et al. ............ 435/288.4 |
| 6,376,233 | B1 | 4/2002 | Wolf et al. |
| 6,602,716 | B1 | 8/2003 | Klimant |
| 6,673,532 | B2 | 1/2004 | Rao |

(Continued)

FOREIGN PATENT DOCUMENTS

EP 1 580 261 A1 9/2005

(Continued)

OTHER PUBLICATIONS

Srinivasan et al., "Micromachined Reactors for Catalytic Partial Oxidation Reactions", AICHE Journal, vol. 43, No. 11, Nov. 1997, pp. 3059-3069.

(Continued)

*Primary Examiner*—Walter D Griffin
*Assistant Examiner*—Bobby Ramdhanie
(74) *Attorney, Agent, or Firm*—Leydig, Voit & Mayer, Ltd.

(57) ABSTRACT

A well plate and its supporting devices provide capabilities found in larger fermenters, such as controlling the oxygen level, the pH level, and temperature of the contents of the well. The well plate includes a plurality of wells, each of which can be independently controlled. Apertures in the wells, for example, provide access for a gas supply and sensors within each well provide data relating to, e.g., oxygen and/or pH level in the well. A control system controls the gas supply for each well based on the information provided by the sensor within the well. Similarly, temperature control elements, such as a heater or cooler, is placed in thermal contact with the interior of the well, as is a temperature measurement element. A control system can independently control the temperature of the contents of the well based on information provided by the temperature measurement element for that well.

14 Claims, 10 Drawing Sheets

U.S. PATENT DOCUMENTS

| | | |
|---|---|---|
| 7,374,725 B2 | 5/2008 | Klein |
| 7,713,486 B2 | 5/2010 | Klein et al. |
| 7,718,134 B2 | 5/2010 | Klein et al. |
| 2002/0025547 A1 | 2/2002 | Rao |
| 2002/0146818 A1 | 10/2002 | Downs et al. |
| 2003/0219360 A1 | 11/2003 | Olivier |
| 2006/0001865 A1 | 1/2006 | Bellalou et al. |

FOREIGN PATENT DOCUMENTS

| | | |
|---|---|---|
| WO | WO 02/26377 | 4/2002 |
| WO | WO 03/093406 A2 | 11/2003 |

OTHER PUBLICATIONS

Michel M. Maharbiz et al., "A Microfabricated Electrochemical Oxygen Generator For High-Density Cell Culture Arrays", Solid-State Sensor, Actuator and Microsystems Workshop, Hilton Head Island, SC, Jun. 2-6, 2002, pp. 259-264.

Liebsch et al "Luminescence Lifetime Imaging of Oxygen, pH, and Carbon Dioxide Distribution Using Optical Sensors" in Applied Spectroscopy vol. 54, No. 4, from 2000.

M.M. Maharbiz, et al., "Microbioreactor Arrays with Parametric Control for High-Throughput Experimentation" Biotechnology and Bioengineering, vol. 85, No. 4, Feb. 20, 2004, p. 376-381.

N. Szita, et al., "Monitoring of Cell Growth, Oxygen, and pH in Microfermentors" in Micro Total Analysis Systems (m-TAS) 2002, Y. Baba, S. Shoji, and A. van den Berg (Eds.). Kluwer, Dordrecht, The Netherlands, 2002, pp. 7-9, as downloaded from http://jensengroup.mit.edu/new_students on Feb. 10, 2004.

Michel Martin Maharbiz, "Electrochemical Gas Generation for Cell Culture", PhD Dissertation, University of California Berkeley, May 2003, pp. 1-98.

Michel Martin Maharbiz, "Electrochemical Gas Generation for Cell Culture", PhD Dissertation, University of California Berkeley, May 2003, pp. 99-170.

Shabbir B. Bambot, et al., "Potential applications of lifetime-based, phase-modulation fluorimetry in bioprocess and clinical monitoring", Tibtech Mar. 1995 (vol. 13), pp. 106-115.

Gerhard J. Mohr et al., "Application of a Novel Lipophilized Fluorescent Dye in an Optical Nitrate Sensor", Journal of Fluorescence, vol. 5, No. 2, (1995) pp. 135-138.

Shabbir B. Bambot et al., "Phase Fluorometric Sterilizable Optical Oxygen Sensor", Biotechnology and Bioengineering, vol. 43, pp. 1139-1145 (1994).

European Search Report dated Mar. 6, 2006, for EP Application No. 05 250 761.1-1521 (4 pgs).

European Examination Report dated Dec. 28, 2006 for EP Application No. 05 250 761.1-1521 (3 pgs).

Response to Examination Report filed Apr. 23, 2007 in EP Application No. 05 250 761.1-1521.

Office Action mailed on Jul. 31, 2009 for U.S. Appl. No. 12/024,973, filed Feb. 1, 2008, by Klein et al., 13 pages.

Response to Office Action dated Oct. 22, 2009 for U.S. Appl. No. 12/024,973, filed Feb. 1, 2008, by Klein et al. (7 pgs).

Office Action mailed on Nov. 13, 2008 for U.S. Appl. No. 12/026,450, filed Feb. 1, 2008, by Klein et al.

Response to Office Action dated Apr. 9, 2009 for U.S. Appl. No. 12/024,973, filed Feb. 1, 2008, by Klein et al. (9 pgs).

Office Action mailed on Jul. 9, 2009 for U.S. Appl. No. 12/026,450, filed Feb. 5, 2008, by Klein et al., 13 pages.

Response to Office Action mailed on Oct. 1, 2009, for U.S. Appl. No. 12/026,450, filed Feb. 1, 2008, by Klein et al., 10 pages.

\* cited by examiner

WELL PLATE REACTOR

CROSS REFERENCE TO RELATED APPLICATION

This application is a continuation of U.S. patent application Ser. No. 12/024,973, filed Feb. 1, 2008, entitled "Well Plate Reactor", now U.S. Pat. No. 7,713,486, which is a divisional application of U.S. patent application Ser. No. 10/777,581, filed Feb. 11, 2004, entitled "Well Plate Reactor," now U.S. Pat. No. 7,374,725, both of which are incorporated herein by reference in their entireties.

FIELD OF THE INVENTION

The present invention relates to reactors, e.g., for cell culture, fermentation, and cell based assays and in particular to well plates and supporting devices.

BACKGROUND

Cell culture and fermentation have value for many aspects of industrial production, such as pharmaceuticals, industrial enzyme production (e.g. detergents, food additives, textile processing, pulp and paper processing, grain processing incl. production of high fructose corn syrup), potable and fuel ethanol, amino acids, vitamins, feed additives, and many others. The actual organisms in the fermenter may vary greatly and can include a variety of bacteria, yeast, fungi, insect cells, mammalian cells, and others.

Conventionally, complex large-scale fermentation (hundreds of thousands of liters) systems are used for production. Large scale systems are manufactured by companies, such as Applikon, B. Braun, and New Brunswick Scientific. Typically, large scale cell culture and fermentation systems must be capable of: 1) feeding the media with nutrients, 2) measuring and changing the Oxygen level, 3) measuring and changing the temperature, 4) measuring and changing the pH level, 4) stifling the contents, 5) purging byproducts (such as $CO_2$), and 6) monitoring the reaction quality (such as cell density and protein expression).

Before scaling up reactions in large capacity fermenters, similar reactions are typically performed at a smaller scale. Small scale fermenters, e.g., in the 1-20 liter range, provide most if not all of the desired performance functions of the large scale fermenters described above. However, the small scale fermenters are expensive, and have a relatively larger form than necessary for many desired applications.

For fermentations on a smaller scale, less expensive systems are typically used. However, conventional inexpensive systems used for very small scale fermentation typically lose several of the desired performance capabilities and, accordingly, quality.

The two most common systems for smaller scale experiments are shake flasks and micro-well plates. Shake flasks are simply glass or plastic vessels that are shaken and supplied with gasses to support the cell growth.

Micro-well plates (which are also called micro-titer plates, well plates or micro plates and will be referred to herein as "well plates") are simply molded plastic plates, with a plurality of wells. A separate fermentation can be performed in each well of a well plate. Well plates typically have a 96 well format, however other well plate sizes also exist (such as 24 well, 48 well, 192 well, 384 well, and 1536 wells). The shape and size of well plates are standardized. The standardization is run by the Society for Bimolecular Screening (SBS).

The main drawback of well plates is that they are typically uncontrolled. While it is possible to run reactions and perform some optical measurements in a conventional well plate, conventional systems do not allow for well-by-well control of conditions in individual wells. Further, many of the desired performance capabilities found in the larger scale fermenters cannot be found in well plates, which inhibits experiments of the quality that are performed in larger fermenters.

By way of example, applications which would be desirable for well plates are drug discovery and diagnostic testing in which cell-based assays are used. Cell-based assays refer to any number of different experiments based on the use of live cells, such as measuring cell proliferation or mortality. There is a recent trend toward more cell-based assays in drug discovery since they are more reliable and robust than biochemical assays. An example of this type of application would be screening compounds for use in cancer therapy. In this case, a particular cancer cell line would be grown under controlled conditions. The growth rate of the cells would be measured after the introduction of a small quantity of test compound. Compounds that kill, or slow or halt growth versus a control are drug candidates. The same approach is used in toxicology screening to assess the potential impact of a compound on different human tissues.

Unfortunately, many cell-based assays are difficult to perform in conventional well plates. The cell lines involved can be quite sensitive to small changes in their environment, resulting in noisy assay output. Other desirable applications, such as diagnostic and clinical tests are likewise difficult to perform in conventional well plates.

Accordingly, what is needed is an improved well plate design and supporting devices that provides, e.g., the performance capabilities of the larger scale fermenters while remaining relatively low cost.

SUMMARY

In accordance with the present invention, a well plate and its supporting instrumentation is used to provide the capabilities typically found in larger fermenters, such as controlling the oxygen level, the pH level, and temperature of the contents of the well. The well plate includes a plurality of wells, each of which can be independently controlled.

In one embodiment of the present invention, a well plate includes a plurality of wells, each well being defined by at least one surface that defines a cavity having an opening. Each well includes at least one aperture through a surface of the well, the aperture being configured to provide a gas supply access to the interior of the well and at least one of a pH level sensor and a dissolved oxygen sensor disposed within the well.

In another aspect of the present invention, a well plate includes a plurality of wells, each well having at least one surface that defines an opening at a top of the well. Each well includes a first aperture through a surface, the first aperture being configured to provide a gas supply access to the interior of the well. Each well includes at least one additional aperture through a surface, the at least one additional aperture being configured to place one of a temperature control element and a temperature measurement element in thermal contact with the interior of the well.

In another aspect of the present invention, an apparatus, for controlling at least one of the pH level and dissolved oxygen in the contents in a plurality of wells in a well plate, each well being defined by at least one surface that defines an opening and has an aperture, includes a gas supply for providing gas to a well through the aperture in the well. The apparatus also includes at least one detector for detecting the pH level and/or the dissolved oxygen in the contents of a well and a control system that is coupled to the gas supply and the detector. The control system controls the amount of gas supplied to the well by the gas supply in response to the detected pH level and/or dissolved oxygen.

In another aspect of the present invention, an apparatus that is used with a well plate having a plurality of well, each well being defined by at least one surface that defines an interior cavity having an opening includes a plurality of drip valves. There is at least one drip valve associated with each well positioned over the opening of each well. The drip valves are configured to provide a liquid to the interior cavities of the associated wells. The apparatus further includes a plurality of detectors for detecting a property of the contents of the wells, wherein there is at least one detector associated with each well and a control system coupled to the plurality of detectors and the plurality of drip valves. The control system controls the amount of the liquid provided by the drip valves to the associated wells in response to the property of the contents in the associated wells detected by the detectors associated with each well.

In another aspect of the present invention, a method includes providing a well plate with a plurality of wells with content in each well. The method includes measuring the pH level and/or the dissolved oxygen in the contents of each well and providing at least one gas to the contents at least one well through a membrane and an aperture in the well in response to the measured pH level and/or dissolved oxygen.

DETAILED DESCRIPTION

In accordance with an embodiment of the present invention, a well plate and supporting instrumentation provides performance capabilities of larger scale fermenters, such as independently controlling the dissolved oxygen and/or pH level in each well and independently controlling the temperature in each well. A well plate in accordance with the present invention may be used for controlling and measuring cell growth, which is useful, e.g., for cell culture, fermentation, and cell based assays.

A well plate and supporting instrumentation, in accordance with the present invention, delivers better control over the micro-environment and thus is more suitable for cell culture, fermentation, and cell based assays than conventional well plates. Improved control over the micro-environment leads to enhanced signal to noise which can generate more reliable results or increase throughput. The use of a system with better control over the micro-environment can also be used downstream of a conventional high throughput screen to validate and refine positive results.

Figure 1:
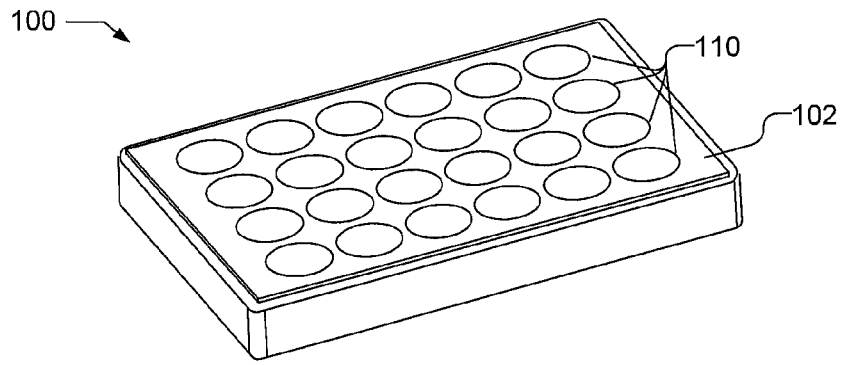
FIGS. 1 and 2 illustrate a top perspective view and a top plan view of a well plate, in accordance with one embodiment of the present invention.
Figure 2:
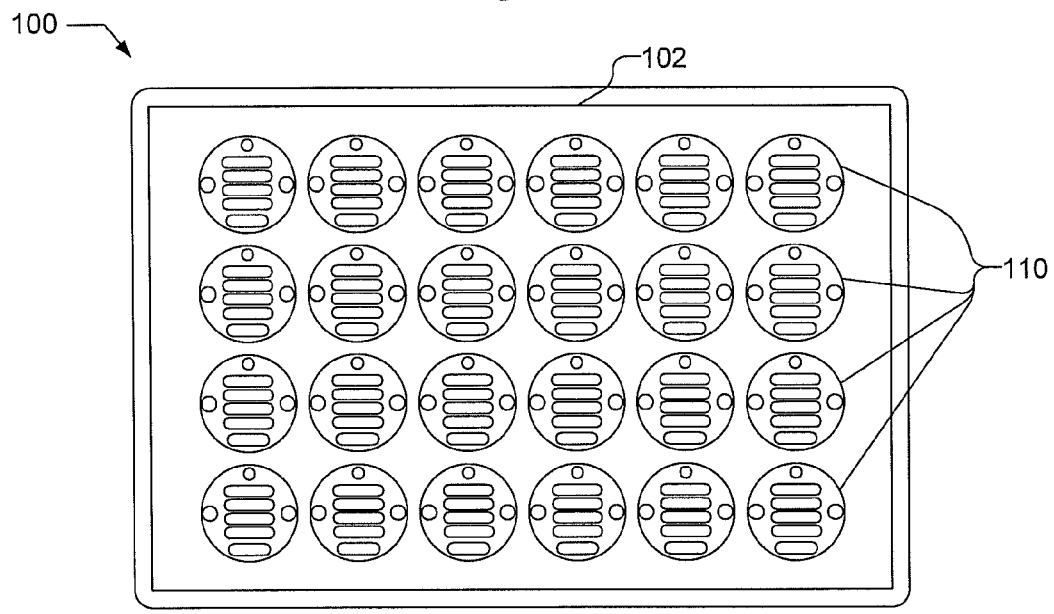

FIGS. 1 and 2 illustrate a top perspective view and a top plan view of a well plate 100 in accordance with one embodiment of the present invention. Well plate 100 is illustrated as having a top surface 102 and a plurality of wells 110, e.g., 24, 48, 96 or any other desired number of wells that extend generally downward from the top surface 102. In general, the dimensions and form of well plate 100 may be similar to the type purchased from Corning Costar from Acton, Mass., as part number #3527 or from Nalge Nunc International from Rochester, N.Y., as part number 142485. Well plate 100 may be manufactured from, e.g., polystyrene, and have a length of 128 mm and a width of 86 mm, with a well volume of 3.4 mL. Of course, many different types of configurations and dimensions may be used with the present invention. By way of example, the well plate 100 may have wells 110 that extend generally upward from a surface rather than extending downward from the top surface 102 as illustrated in FIG. 1.

It should be understood that while FIGS. 1 and 2 illustrate the wells 110 as round, other geometries may be used if desired. For example, wells 110 may be, e.g., square, which advantageously offer more volume and better mixing due to turbulence from the corners. The bottom surface of the wells 110 is generally flat, but a round well bottom may be used as well, e.g., the well 110 may have a generally semi-spherical shape. Moreover, the depth of the wells may be varied, which provides additional well volume with a fixed well plate footprint.

Figure 3A:
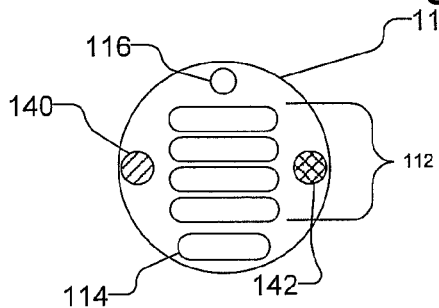
FIGS. 3A and 3B are views of the interior bottom surface of different embodiments of a well.

FIG. 3A is a view of the interior bottom surface of one well 110. As can be seen in FIGS. 2 and 3A, each well 110 includes a plurality of apertures. The apertures in the bottom surface of each well 110 provide access for temperature measurement and control and the dissolved oxygen and pH control for each well.

In one embodiment, a plurality of apertures 112 are located in the approximate center of the each well 110 and are used provide a gas to the well 110. The gas that is provided through apertures 112 are used to control the dissolved oxygen and pH level of the contents of the well. The gas is supplied through apertures 112 through a membrane that may be located on the exterior bottom surface of the well 110. In some embodiments, the membrane may be located on the interior bottom surface of the well 110. The membrane and gas supply in general will be discussed in more detail below. The central apertures 112 are illustrated as rectangular with rounded corners, however, other dimensions may be used. The central apertures 112 may be considered a single large aperture with a series of support ribs, which advantageously limit the deformation of the external membrane during the gas exchange.

Figure 3B:
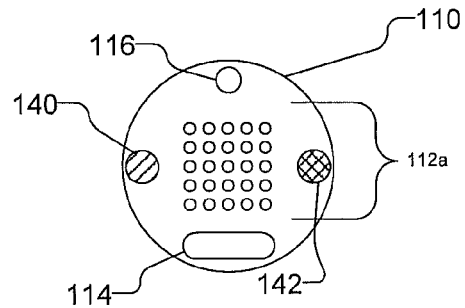

FIG. 3B is a view of another embodiment of the interior bottom surface of a well 110. As can seen in FIG. 3B, the gas supply apertures 112a is an array of circular apertures, e.g., that are 0.2 to 1.0 mm in diameter and spaced approximately 1 mm to 2 mm apart. The use of an array of apertures 112a is particularly useful to control the number of bubbles and bubble size during the supply of gas when a porous membrane is used.

Each well also includes two additional apertures 114 and 116, which are used to provide thermal contact between the interior of the well 110 and a heater element and temperature measurement element through the membrane. As illustrated in FIG. 3A, the apertures 114 and 116 are located on opposite sides of the well 110 to maximize their distance and to minimize local localized heating errors. Heating and temperature measurements of the contents of a well 110 will be discussed in more detail below.

The apertures 112, 114, and 116 may be formed in the bottom of the well plate 100 using conventional cutting techniques such as water jet cutting or laser, which is particularly useful when the well plate 100 is manufactured from a plastic. If desired, other cutting techniques may be used, such as conventional machining. Further, if desired, the well plate 100 may be custom molded, which obviates the need for cutting the apertures in the bottom of the wells 110.

In addition, each well 110 includes one or more sensors to measure the dissolved oxygen and/or the pH level. The measurement of dissolved oxygen and/or pH level in each well 110 may be used to control the control the supply of gas to the well 110, e.g., in a feedback loop. In one embodiment, the sensors are integrated into the well plate 100 as illustrated in FIGS. 3A and 3B. By way of example, an oxygen sensor 140 and a pH sensor 142 are deposited on the interior bottom surface of the well 110. The sensors 140 and 142 may be, e.g., fluorescent tags. The sensors can be deposited as small dots that are approximately 50 μm thick and 2 mm in diameter. The use of fluorescent tags as integrated sensors in well plate 100 is advantageous as they are inexpensive, and do not require significant calibration.

The chemicals used to produce the fluorescent tag for oxygen sensor 140 may be purchased from, e.g., Aldrich or Precision Sensing GmbH, located in Germany. The dissolved oxygen sensor may be based, e.g., on an organic indicator, or if desired based on Tris (4,7-diphenyl-1,10-phenanthrolin) ruthenium(II).

The chemicals used to produce the fluorescent tag for pH sensor 142 may be purchased from Precision Sensing GmbH. An adequate pH sensor and measuring technique is described in U.S. Pat. No. 6,602,716, which is incorporated herein by reference. In an alternative embodiment, a dye such as a pH sensor dye that is embedded into a film may be deposited within the well 110. By way of example, a die that is embedded into a film may be purchased from Precision Sensing GmbH or Molecular Probes, Inc. of Eugene Oreg.

If desired, additional sensors may be used with well 110. Thus, each well 110 may include more than two sensors 140 and 142. By way of example, fluorescent sensors that measure $CO_2$ sensors and glucose may be included within the wells 110.

Figure 4:
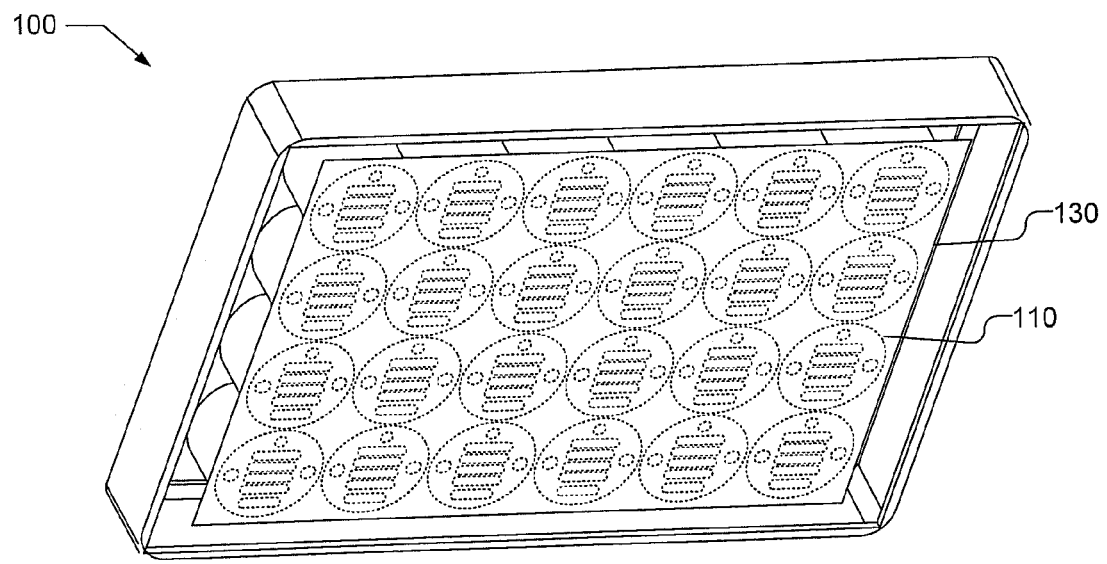
FIG. 4 illustrates a perspective view of the bottom of the well plate with a membrane attached to the exterior bottom surfaces of the wells.

FIG. 4 illustrates a perspective view of the bottom of the well plate 110 with a membrane 130 attached to the exterior bottom surfaces of the wells 110 (the bottom of the well 110, with its apertures and the dissolved oxygen and pH sensors on the interior bottom surface of the wells are shown with broken lines). The membrane 130 is a highly permeable thin membrane through which gasses can be easily passed. The membrane 130 may be precut to fit over all the wells 110 in one piece, or multiple pieces of membrane may be used to cover one or more wells. The membrane 130 is attached to the well plate 100, e.g., with a silicon pressure adhesive or other appropriate adhesive. Alternatively, the membrane 130 may be attached by ultrasonic or thermal bonding, such as that produced by Toman Tool Corporation. In one embodiment, the membrane 130 includes openings that are associated with the sensors 140 and 142 of each well 110 so as to minimize interference.

By way of example, the membrane 130 may be manufactured from silicone or siloxane polymer. Alternatively, the membrane 130 may be made from a blend of siloxane and a thermoplastic such as polycarbonate to increase robustness. The use of the rectangular central apertures 112, illustrated in FIG. 3A, is particularly useful with a silicon membrane. Adequate silicone or siloxane polymer membranes may be purchased, e.g., from Specialty Silicone Products, located in Ballston Spa, N.Y. The particular membrane 130 will depend on the desired permeability. By way of example, a membrane that is 50 μm thick may be used, which has a permeability that is approximately thirty times better than carbon based polymers. Such a 50 μm thick membrane would provide, e.g., $4 \times 10^{-4}$ mol of oxygen per hour in each well, where the exposure area is 5 $cm^2$ and a 10 psi gas pressure is used. With the presence of water on one side of the membrane 130, e.g., in the well 110, the supply of oxygen may be reduced, but will still be several times higher than necessary for a vigorous fermentation in the approximately 1 ml of volume in each well 110. The use of a permeable membrane is advantageous for gas transfer as the oxygen goes directly into solution and, thus, no bubbles are formed and lost through the top of the well. Thus, a permeable membrane is useful for low flow experiments over an extended time period.

Where reactions require higher gas fluxes, a porous membrane 130 may be used, e.g., a membrane that includes small holes. The use of the array of circular apertures 112a, illustrated in FIG. 3B, is particularly useful with a porous membrane. By way of example, a membrane that includes holes less than 0.2 μm may be used. Liquid cannot pass through holes of this size nor can microbes that could contaminate the fermentation. In general sterile filtration calls for a pore size of less than 0.2 μm. Manufacturers of useful membranes include W.L. Gore & Associates, located in Newark Del., Porex Corporation located in Fairburn, Ga., and Mitsui Chemicals, Inc. located in Japan. By way of example, a 0.2 μm (or smaller) pore size membrane from a material called ePTFE that is laminated with a polyester support and manufactured by W.L. Gore & Associates may be used. The polyester support is useful to provide strength and it is able to withstand gamma irradiation, which is used to sterilize the well plate 100. Porous membranes are particularly advantageous where a high gas transfer rate is desired. Moreover, because of the high gas transfer rate, bubbling will occur which is useful in stifling the reactor volume. However, because bubbling may result in splashing and foam generation, an anti-foaming agent may need to be added to the fermentation.

Figure 5A:
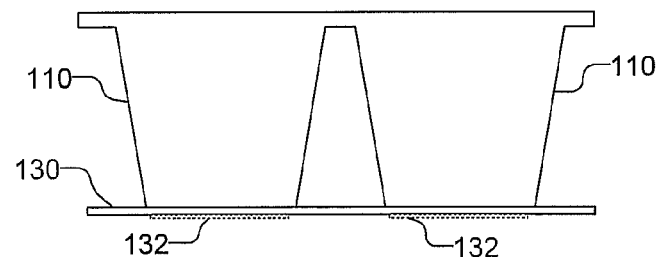
FIG. 5A illustrates a side view of two wells with a laminate membrane structure.

In one embodiment of the present invention, a laminate of two membranes or a one membrane and another material, such as polyester, may be used at the same time. FIG. 5A illustrates a side view of two wells 110 with a first membrane 130 and a second material 132, which may be another membrane, attached to the exterior bottom surface of the wells 110. In one embodiment, the first membrane 130 is a porous membrane that is relatively thick and thus may be used as support for the second membrane 132. The second membrane 132 may be, e.g., a thin coating that is applied to the first membrane 130 to seal the membrane. The second membrane 132 may be applied locally at the bottom of each well 110 or over the entire surface of the first membrane 130. The use of a second membrane 132 or a coating on the first membrane 130, produces a structure that behaves like a non-porous membrane but that can achieve a high gas transfer rate thane with thicker polymer membranes.

Figure 5B:
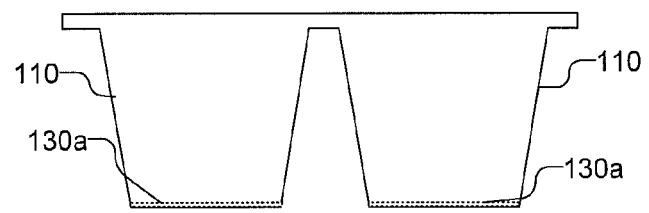
FIG. 5B illustrates a side view of two wells with membranes attached to the interior bottom surface of the wells.

It should be understood that the membrane may have alternative configurations. For example, instead of a large sheet of membrane that covers the entire bottom of the well plate 110 as illustrated in FIG. 4, the membrane may be formed from individual disks, where each disk covers the exterior bottom surface of an individual well 110. Alternatively, the membrane may be individual disks that are inserted into individual the well to cover the interior bottom surface of the well. FIG. 5B illustrates a side view of two wells 110 with membranes 130a attached to the interior bottom surface of the wells 110. The membranes 130a may be similar to the membranes discussed above and may be ultrasonically or thermally bonded to the wells 110. If desired other bonding techniques may alternatively be used, such as a silicon pressure adhesive. Alternatively, the membrane may be formed by individual disks that are partially embedded into the bottom surface of the well 110. For example, the bottom surface of the well 110 may include a counter bore into which an individual membrane is mounted. The use of a counter bore in the well would countersink the membrane.

Additionally, multiple membranes may be used for different portions of an individual well 110. For example, a thin highly porous membrane may be used to cover the apertures 112 for the gas supply to the well, while a thicker, more robust membrane, e.g., that is optimized for thermal transfer, may be used to cover apertures 114 and 116 for heater element and temperature measurement element. Alternatively, a single membrane having different thicknesses may be used. By way of example, a portion of a silicone membrane that covers the gas supply apertures 112 may be relative thin while the portion of the same membrane that covers apertures 114 and 116 (which are used to provide thermal contact between the interior of the well 110 and a heater element and temperature measurement element) may be relatively thick.

Once the well plate 100 is formed, including the formation of the apertures and the sensors in the well 110, the well plate 100 is sterilized, e.g., by exposing the well plate to gamma radiation or ethylene oxide.

Figure 6:
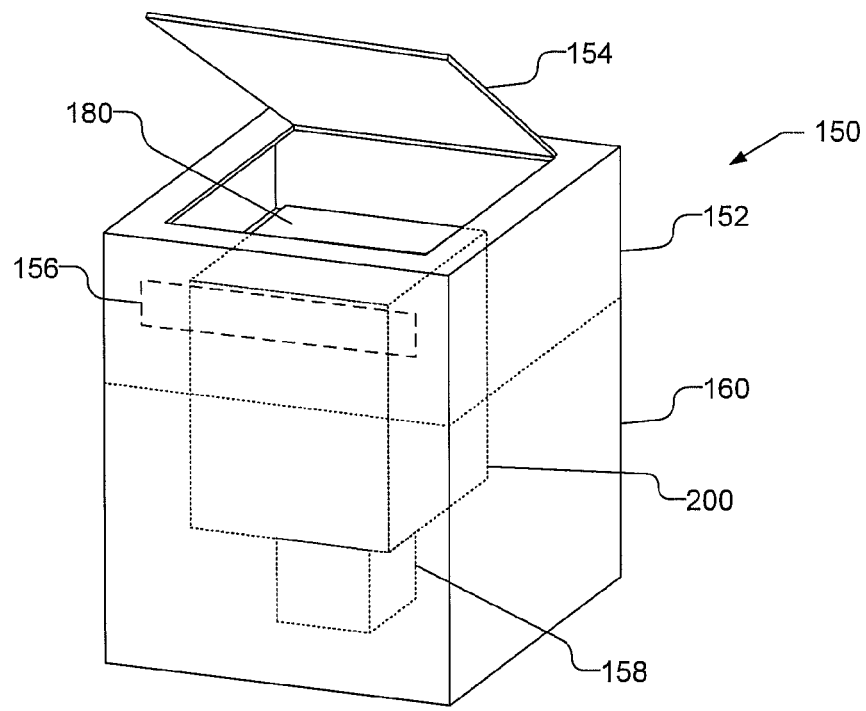
FIG. 6 shows a block diagram of a device that may be used with well plate to control the culture and/or fermentation of the contents of the wells.

FIG. 6 shows a block diagram of a device 150 that may be used with well plate 100 to controls the culture and/or fermentation of the contents of the wells. The device 150 includes a compartment 152 in which the well plate 100 is inserted, e.g., through a top door 154 or through a side door 156. A robotic arm (not shown) may be used to assist in placing the well plate 100 in the compartment 152. The well plate 100 is clamped down on an instrumentation block 200, which will be discussed in more detail below. The environment within the compartment 152 is controlled, e.g., using a gas vent, a TEC based heater/cooler, and a humidifier. In addition, the device 150 may include an agitator 158 that moves the well plate 100 and instrumentation block 200 in, e.g., an orbital pattern. The compartment 152 is separated from an electronics compartment 160 by a bellows, e.g., between the instrumentation block 200 and the walls of the device 150, which permits the well plate and instrumentation block 200 to move and contains the desired environment within the compartment 152, thereby avoiding condensation and other problems with sensitive optics and electronics contained within the electronics region 160. In general, controlling the environment within a chamber, such as compartment 152 and providing agitation to an element within the chamber, is well within the abilities of those skilled in the art. The device 150 may include a user interface (not shown) that is, e.g., coupled to the control system for the device and permits the user to provide input and provides feedback to the user.

Figure 7:
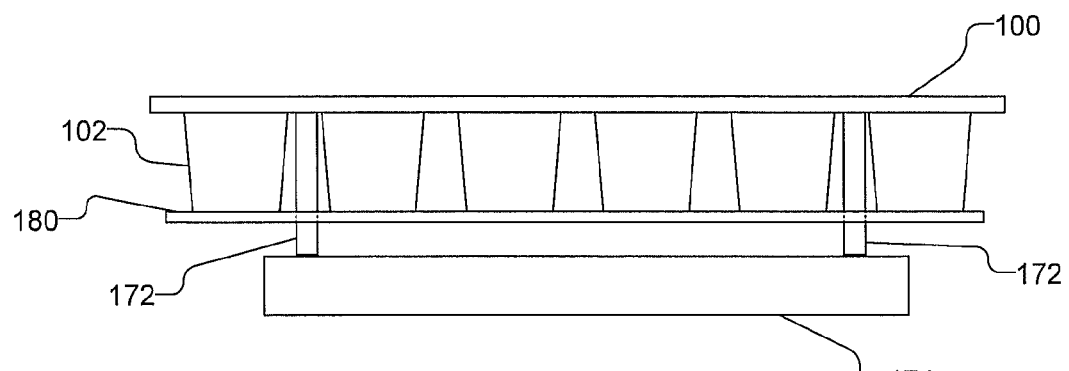
FIG. 7 illustrates a side view of one embodiment of vacuum clamping the well plate.

FIG. 7 illustrates a side view of one embodiment of vacuum clamping the well plate 100 to a top surface of the instrumentation block 200. A number of pipes 172, e.g. four, extend from a vacuum pump 174 to a flat surface of the well plate 100. The pipes 172 may include rubber gaskets at the top surface to provide a seal with the well plate 100. When the vacuum is applied to the well plate 100, the bottom surfaces of the wells 110 are placed in firm contact a top surface 180 of the instrumentation block 200. It should be understood that the pipes 172 extend through the membrane 140, which is not shown in FIG. 7. Of course, other methods of clamping the well plate 100 to the instrumentation block 200 may be used if desired, such as by mechanical clamping.

Figure 8:
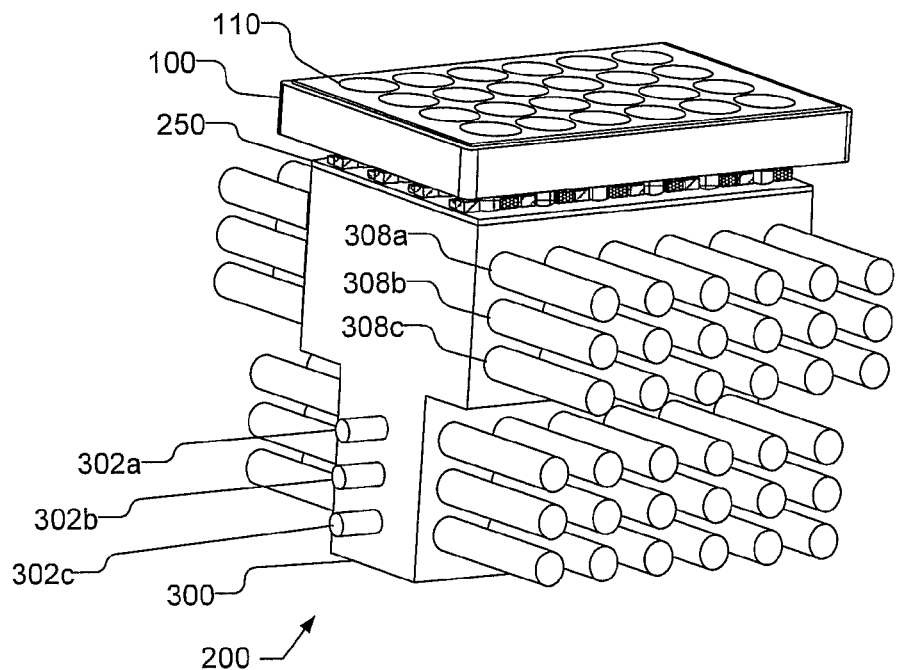
FIGS. 8 and 9 illustrate a perspective view and side view, respectively, of a well plate mounted on an instrumentation block.
Figure 9:
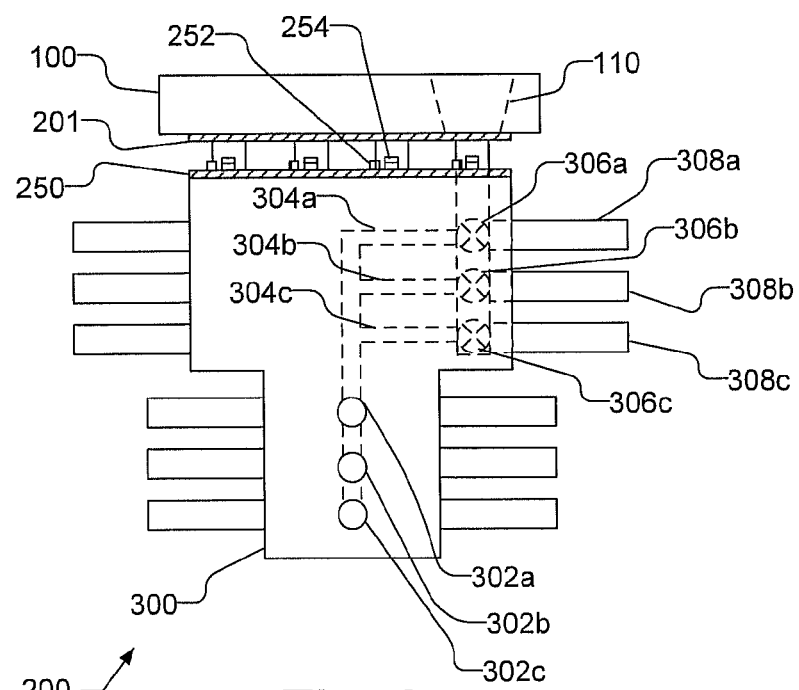

FIGS. 8 and 9 illustrate a perspective view and side view, respectively, of a well plate 100 mounted on the instrumentation block 200. The top surface of the instrumentation block 200 to which the well plate 100 is clamped is a support plate 201. The support plate 201 creates a seal with the well plate 100 and also provides the temperature control elements, i.e., a heating/cooling element and a temperature measurement element. An optical plate 250 is positioned below the support plate 201 and includes optical devices that are used to measure the dissolved oxygen and/or pH level using the sensors 140 and 142. Below the optical plate 250 is a gas manifold 300, which is illustrated schematically in FIGS. 8 and 9. Manifold 300 is used to control the flow of gas to the individual wells 110 in the well plate 100.

Figure 10:
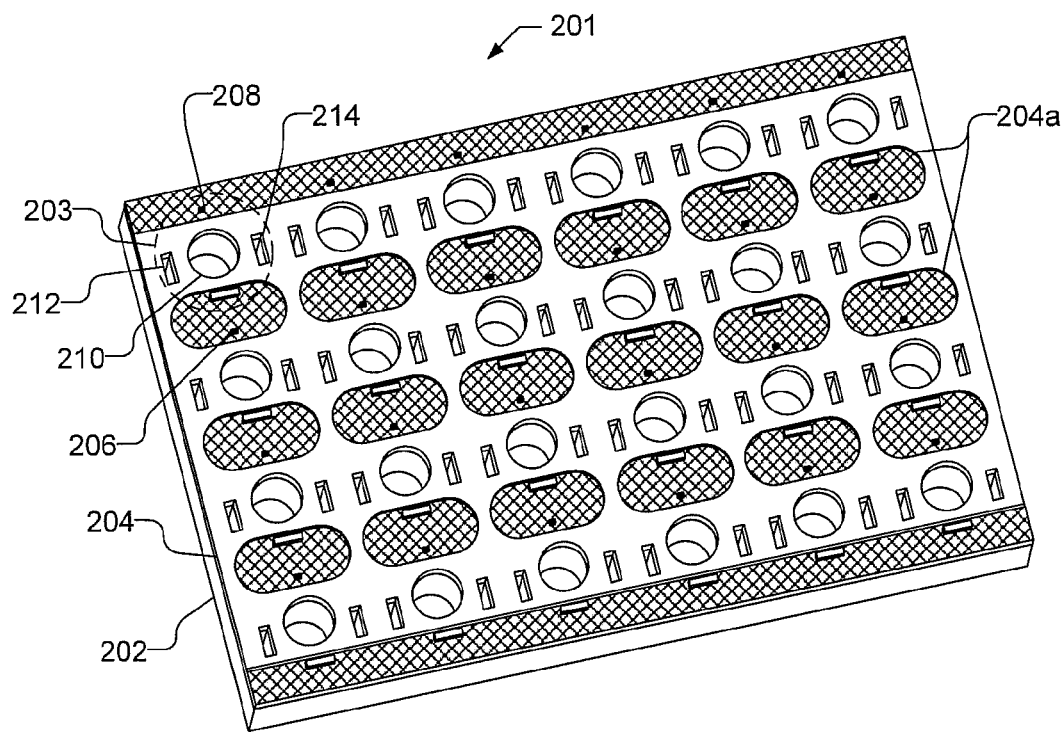
FIG. 10 illustrates a top perspective view of a support plate used in the instrumentation block.

FIG. 10 illustrates a top perspective view of a support plate 201. In use, the support plate 201 is robustly mounted to the gas manifold 300 with mount hardware such as bolts. The gas manifold then pulls the well plate 100 down onto the support plate 201 by vacuum or other comparable clamping methods, as discussed above. As can be seen in FIG. 10, support plate 201 includes a plurality of similarly configured areas, each of which is associated with a separate well 110 of the well plate 100. For the sake of clarity, the footprint of the bottom of a well 110 when the support plate 201 is clamped to the well plate 100 is illustrated with a dotted line 203 in FIG. 10.

The support plate 201 is, e.g., a printed circuit board 202 that has a gasket 204 mounted on the top surface, e.g., with adhesive. The gasket 204 provides a gas-tight seal with the well plate 100 when the support plate 201 is clamped into contact with the bottom of the well plate 100 through the membrane 130. The support plate 201 also includes a plurality of heating elements 206 and temperature measurement elements 208 on the top surface, where a pair of heating elements 206 and temperature measurement elements 208 is associated with each well 110. Thus, for example, where the well plate 100 has 24 wells 110, the support plate 201 includes 24 pairs of heating elements 206 and temperature measurement elements 208. As illustrated in FIG. 10, the gasket 204 is trimmed to expose the heating elements 206 and temperature measurement elements 208, which are mounted on the printed circuit board 202. By way of example, the gasket 204 may includes cut out sections 204a to expose the underlying heating elements 206 and temperature measurement elements 208. Additionally, the gasket 204 may not extend to the sides of the board 202, again to ensure that the heating elements 206 and temperature measurement elements 208 are not covered.

The heating elements 206 may be, e.g., resistive heater elements. Where cooling of the contents of the well is desired, the heater elements 206 may be Peltier coolers (TEC cooler) instead of resistive heater elements. Thus, the elements 206 may be used to heat or cool the contents of the wells 110, the elements 206 will sometimes be referred to as temperature control elements. The temperature measurement elements 208 may be, e.g., thermistors.

It should be understood that while the device 150 (shown in FIG. 6) controls the temperature of the overall compartment 152, the heating elements 206 and temperature measurement elements 208 are used to independently control the temperature within the individual wells 110.

As can be seen in FIG. 10, the support plate 201 also includes a central aperture 210, and two side apertures 212 and 214 through both the printed circuit board 202 and the gasket 204. When properly positioned, the central apertures 210 are aligned with the center apertures 112 in each well 110. The side apertures 212 and 214 provide optical access to the sensors 140 and 142 from the optics plate 250, which is positioned below the support plate 201. Thus, when properly positioned, apertures 212 and 214 are positioned under the oxygen sensor 140 and a pH sensor 142 in each well 110.

Figure 11:
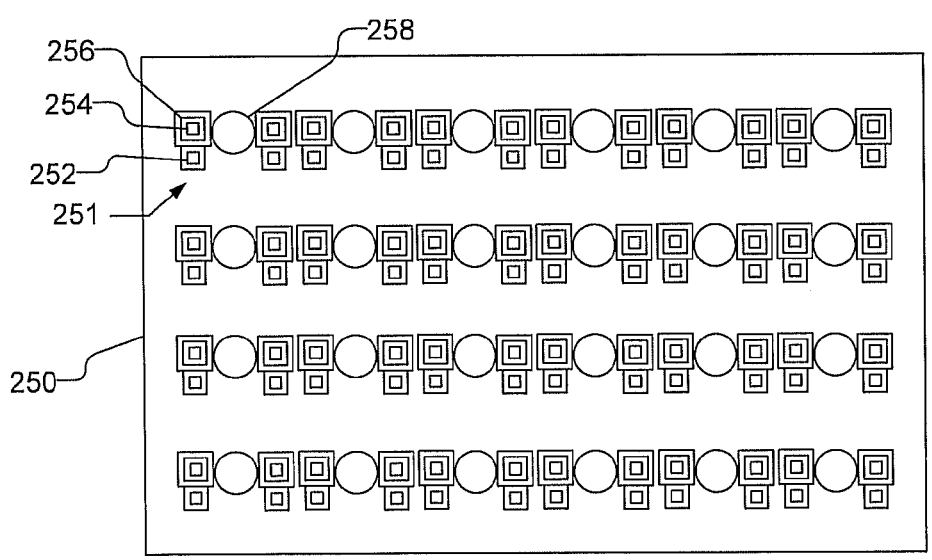
FIG. 11 is a top plan view of the optics plate used in the instrumentation block.

FIG. 11 is a top plan view of the optics plate 250. Optics plate 250 includes a plurality of detection heads 251 that are used in conjunction with the sensors 140 and 142 to measure the dissolved oxygen and pH level of the contents in a well. By way of example, each detection head includes a light emitting diode (LED) 252 and a photodiode 254, and a separate detection head is provided for each sensor in the well plate 100. By way of example, the detection heads 251 may use and a Nichia blue-green LED (NSCE310T) (505 nm) for the oxygen sensor 140, a Nichia Blue LED (NSCB310T) (470 nm) for the pH sensor 142, and a Hamamatsu S8729-10 photodiodes. A wavelength filter 256 may be mounted over each photodiode 254. By way of example, the detection heads 152 may use a color glass long pass filter that is 1 mm thick and for the oxygen sensor 140 may be, e.g., RG630, which passes light of wavelengths longer than 630 nm and for the pH sensor 142 may be, e.g., OG530, which passes light of wavelengths longer than 530 nm.

When properly positioned, the LED 252 and photodiode 254 are aligned with the aperture 212 or 214 and the corresponding sensor 140 or 142 in the well 110. In addition, optics plate 250 includes an aperture 258 that is aligned with central apertures 210 of the support plate 201.

To measure the dissolved oxygen and pH level in the contents of a well, the decay lifetime of the fluorescent oxygen sensor 140 and a pH sensor 142 in the well 110 is measured, which corresponds to the amount of dissolved oxygen and pH level. Measurement of the time response of the sensors 140 and 142 is performed by, e.g., pulsing light from the LED 252. For example, the decay lifetime can be measured to determine the dissolved oxygen content. The pH level can be determined by measuring the intensity ratio between a short lifetime pH indicator and a long lifetime reference indicator.

The pulsed light may be, e.g., a square wave on-off measurement profile may be used with approximately 1 kHz for the oxygen sensor 140 and approximately 8 kHz for the pH sensor 142. It is desirable for the period of the square wave to be much greater than the lifetime of decay lifetime being measured. Models indicate that the use of a square wave with a period that is approximately 20 times greater than the decay lifetime being measured provides an error of approximately 1% or less. The square wave is generated using digital techniques, such as using an oscillator circuit with a divider circuit to divide down the oscillations to the desired frequency. Alternatively, a sine wave may be used. The use of a square wave, however, provides a stable frequency, which is relatively difficult to do with a sine wave. Moreover, because a square wave is "on" and "off", the use of a square wave advantageously avoids problems associated with LED non-linearities.

In general, the fluorescent sensors absorb the incident light and emit light with a different wavelength after a delay that corresponds to the decay lifetime. The light emitted from the sensors is then detected by the photodiode 254 and the phase shift between the incident light and the emitted light can then be measured. The filter 256 ensures that the photodiode 254 receives only light emitted from the associated sensor and not light from the LED 252. If desired, instead of measuring the decay lifetime, the intensity of the light emitted from the fluorescing sensors may be measured. However, measuring the intensity of the resulting light requires calibration to account for thickness, density and efficiency variations.

The response in the photodiode 254 is measured using a conventional "lock-in" detector, which is well known in the art. Lock-in detection is commonly performed with an I-Q demodulator circuit, in which two signals are generated. One signal is the in-phase (I) signal and the other signal is the quadrature (Q) signal. The amplitude of the signal that is in phase (I) relative to a reference signal is measured along with the amplitude of the signal that is 90 degrees out of phase, i.e., the quadrature (Q) signal, relative to the reference signal. The I and Q measurements can then be used to determine, e.g., the amplitude and the phase shift, e.g., using analog electronics or simply by digitizing and processing the signal at a high rate (e.g., 10 MHz) in a computer or digital signal processor.

With the use of a square wave signal, where the lifetime being measured is much shorter than the period of the square wave, the dissolved oxygen content can be determined by the following:

$$\text{Amplitude} = 2 * (I + Q) \qquad \text{eq. 1}$$

$$\text{Lifetime}(\tau) = \frac{T}{4\left(\frac{I}{Q} + 1\right)} \qquad \text{eq. 2}$$

where I is the in phase signal, Q is the quadrature signal, and T is the period of the square wave. Using the lifetime ($\tau$) for the dissolved oxygen signal, the dissolved oxygen or pH level can be determined using the Stern Volmer equation, which is expressed as follows:

$$\frac{\tau_0}{\tau} = 1 + K_{SV}[O_2] \qquad \text{eq. 3}$$

where $\tau_0$ are the intrinsic lifetime (no oxygen quenching) fluorescent lifetime for the particular sensor fluorophore and $K_{SV}$ describes a simple linear relationship with the quenching and the oxygen concentration. If desired, modified Stern Volmer equations may be used, which are well known in the art.

The pH sensor 142 includes an indicator material and a reference material, which have different lifetimes for decay. The lifetime of decay for the indicator material is a function of pH level, while the lifetime of decay of the reference material does not vary. With the use of a square wave, the pH level can be determined by the following:

$$\text{Ratio of indicator to reference} = \frac{4\tau_{ref}}{T}\left(\frac{I}{Q}+1\right)-1 \qquad \text{eq. 4}$$

where $\tau_{ref}$ is the lifetime of the decay for the reference material. A description of the pH material and the use of the ratio of indicator to reference to determine pH level can be found in U.S. Pat. No. 6,602,716, which is incorporated herein by reference.

Figure 12:
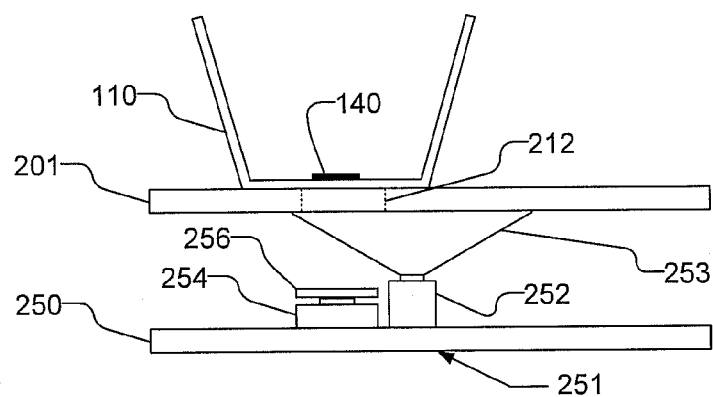
FIG. 12 illustrates a side view of a well with a sensor and a detection head.

FIG. 12 illustrates a side view of a well 110 with a sensor 140, a portion of the support plate 201 and a portion of the optics plate 250 with a detection head 251 including an LED 252 and photodiode 254. As can be seen, the LED 252 may be offset from the sensor 140 slightly. The light emitted by LED 252, illustrated by cone 253 is incident on sensor 140 after passing through aperture 212 in the support plate 201. Light that is emitted by the sensor 140 is received by photodiode 254 after passing through filter 256. The detection head used with the pH sensor 142 may be similarly positioned. Alternatively, the LED 252 may be angled on the optics plate 250 so that the emission is centered on the sensor 140.

Figure 13A:
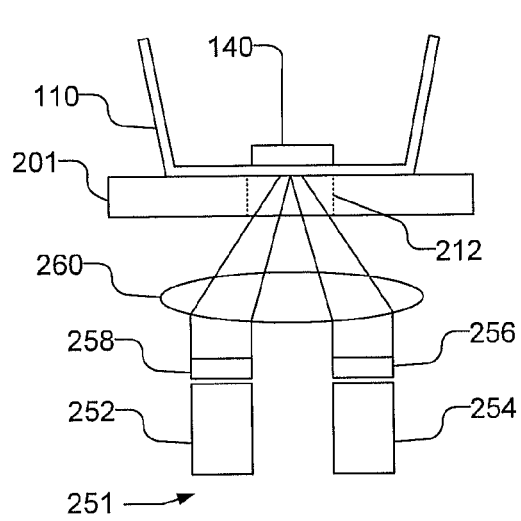
FIGS. 13A and 13B illustrate embodiments of the detection head.
Figure 13B:
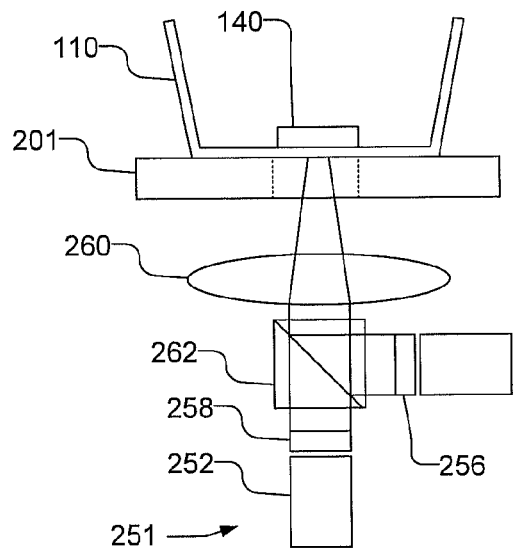

It should be understood that other embodiments of the detection heads 251 may be used. By way of example, FIG. 13A illustrates an embodiment, in which a lens 260 is used to focus the light on the sensor 140. A filter 258 may be used with the LED 252 if desired, e.g., if the emission profile of the LED is too broad. By way of example, a short pass or band pass filter 258 may be used. FIG. 13B illustrates another embodiment, in which a beam splitter 262 is used with the detection head 251.

Figure 14:
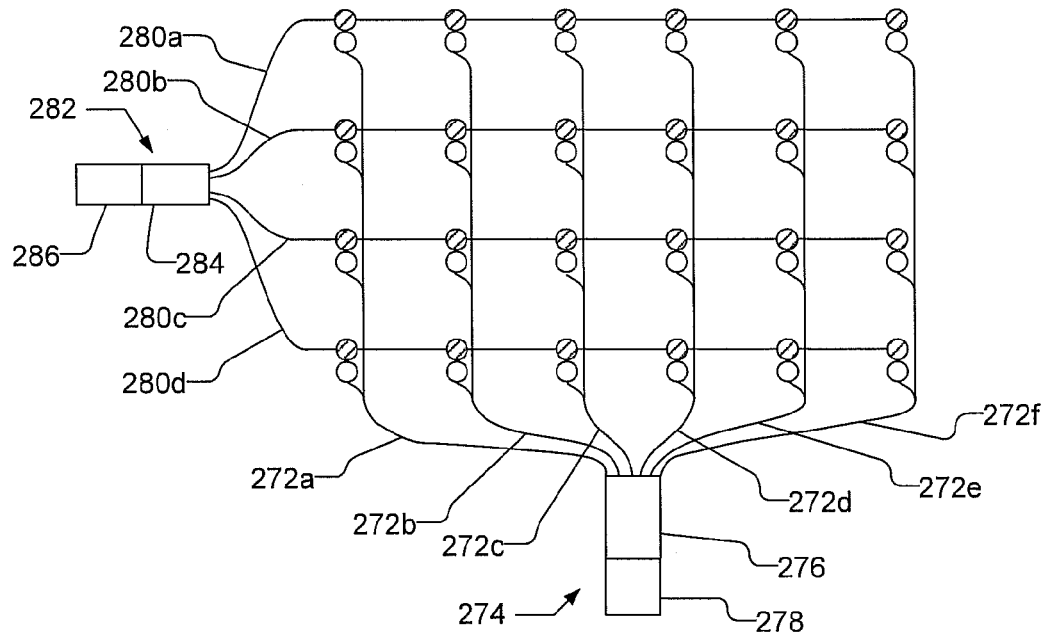
FIG. 14 illustrates a top plan view of a detection head that uses optical fibers and multiplexers.

In another embodiment, optical fibers may be used with the detection heads. FIG. 14 illustrates a top plan view of the use of a plurality of optical fibers 272a, 272b, 272c, 272d, 272e, and 272f that extend from a light source 274 that includes a multiplexer 276 and LED 278 to locations under each sensor in the wells. The optical fibers may be plastic optical fibers that are, e.g., 1 mm to 2 mm in diameter. It should be understood that for a system with 24 wells with two sensors per well, FIG. 14 shows only half of the necessary fibers. Optical fibers 280a, 280b, 280c, and 280d extend from locations under each sensor in the wells to a detector 282 that includes a multiplexer 284 and a photodiode 286. The detector 282 may also include a filter. By multiplexing the light source 274 to the different columns and the detector 282 to the different rows, each sensor can be individually examined. Of course, if desired, the multiplexers 276 and 284 may be eliminated by using a dedicated LED and/or photodiode onto each fiber.

Figure 15:
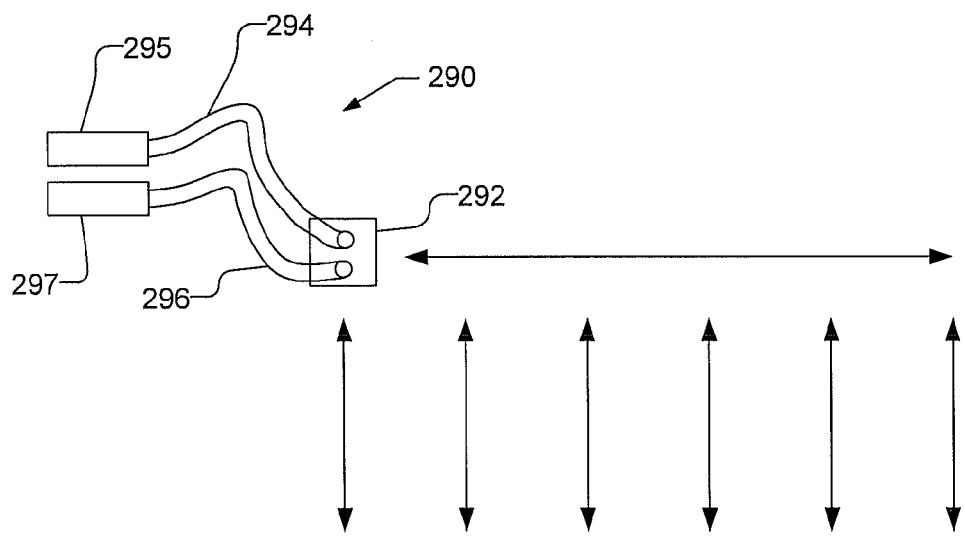
FIG. 15 illustrates an embodiment of a detection head that uses a two dimensional stage.

In another embodiment, a single detection head 290 may be used with a two dimensional stage 292 as illustrated in FIG. 15. Optical fibers 294 and 296, which are coupled to an LED 295 and photodiode 297 respectively are mounted on the two dimensional stage 292. The stage 292 moves the fibers as illustrated in FIG. 15 to separately examine each sensor in the well plate 100.

Referring back to FIGS. 8 and 9, gas is supplied to the wells 110 of the well plate 100 through a manifold 300. The manifold includes gas inputs 302a, 302b, and 302c (collectively 302), through which the desired gas is supplied to the manifold 300. As illustrated in FIG. 9, within the manifold 300, separate gas lines 304a, 304b, 304c (collectively 304) are routed from the gas inputs 302 to valves 306a, 306b, and 306c (collectively 306). It should be understood that, although FIG. 9 illustrates the lines overlapping in sections, the gas lines 304a, 304b, and 304c are all separate lines. The valves 306 are operated by solenoids 308a, 308b, and 308c (collectively 308), which may be purchased from Bio-Chem Valve, Inc., located in Boonton, N.J., or Pneutronics division of Parker. Alternatively, micro-electro-mechanical systems (MEMs) based valves may be used, such as that manufactured by Redwood Microsystems.

The manifold 300 may include an internal or external filtration and regulation system. By way of example, the manifold may include a filter to filter the incoming gas and a regulator to regulate the gas supply, e.g., to between 5-20 psi. By way of example, the gas supply may be regulated to 5 psi when a porous membrane is used and to a higher psi, e.g., 20 psi, when a silicone membrane is used. The manifold 300 may also include a flow limit valve on the gas input lines to limit the maximum flow rate of the gas, e.g., to between 0.01 sccm to 1.0 sccm. In addition, a check valve may be included to prevent contamination of the gas supply from back flow from the wells if a membrane were to malfunction. In one embodiment, the regulator and flow limit valve are adjustable, e.g., through a computer interface or mechanically, so that well plates 100 with different types of membranes may be used with the device 150.

From the valves 306, a single gas line 310 extends to the top surface 312 of the manifold 300, through the central aperture 258 in the optics plate 250, through the center aperture 210 in the support plate 201 and to the bottom of a well 110. The gas that is provided through the gas line 310 passes through the membrane 130 and into the well 110 through apertures 112 in the bottom of the well 110.

It should be understood that FIG. 9 illustrates only one set of gas lines for a well 110. The manifold 300 includes separate gas lines 304/310, valves 306, and solenoids 308 for each well 110 in the well plate 100 so that the supply of gas to each well can be independently controlled.

By way of example, one gas line 302a may supply oxygen which will alter the dissolved oxygen in the contents in a well 110. The oxygen may be supplied as pure oxygen or as compressed air. Compressed air is advantageous because it is inexpensive and non-flammable. However, compressed air includes only 20% oxygen and thus, a greater volume of gas must be provided to the well 110 in order to provide the desired amount of oxygen.

Another gas line 302b my supply $CO_2$ which is used to control the pH level of the contents in a well 110. The $CO_2$ will drive the solution acidic as it forms carbonic acid in an aqueous solution. Another gas line 302c may supply $NH_3$, which is also used to control the pH level of the contents in a well 110. The $NH_3$ will drive the solution basic. The $NH_3$ may be supplied, e.g., as either pure ammonia gas or diluted (10:1) with nitrogen, which is commonly done for safety.

Other gases may also be supplied, such as nitrogen or other inert gases that can be used to purge the wells of oxygen in a low-oxygen application, e.g., by bubbling the inert gas through the contents of the well, or to provide bubbling action without introducing chemically active elements. Additionally, methane and/or hydrogen may also be provided. Of course, other gases may be provided if desired.

It should also be understood that while FIGS. 8 and 9 illustrate three valves 306 per well 110, fewer valves may be used if desired. For example, one valve may be used for controlling the oxygen/air supply, while a second valve may be used to control either $CO_2$ or $NH_3$. By way of example, the oxygen/air supply may be provided through apertures 112 in the bottom of the well 110, while pH regulation may be accomplished using a micro-valve to drip in dilute NaOH or acid.

It should be understood that other methods may also be used to supply gas to the wells 110. For example, chemical reactions, electrolysis, and thermal devolution, in which an element releases gas as it is heated, may be used.

Figure 16:
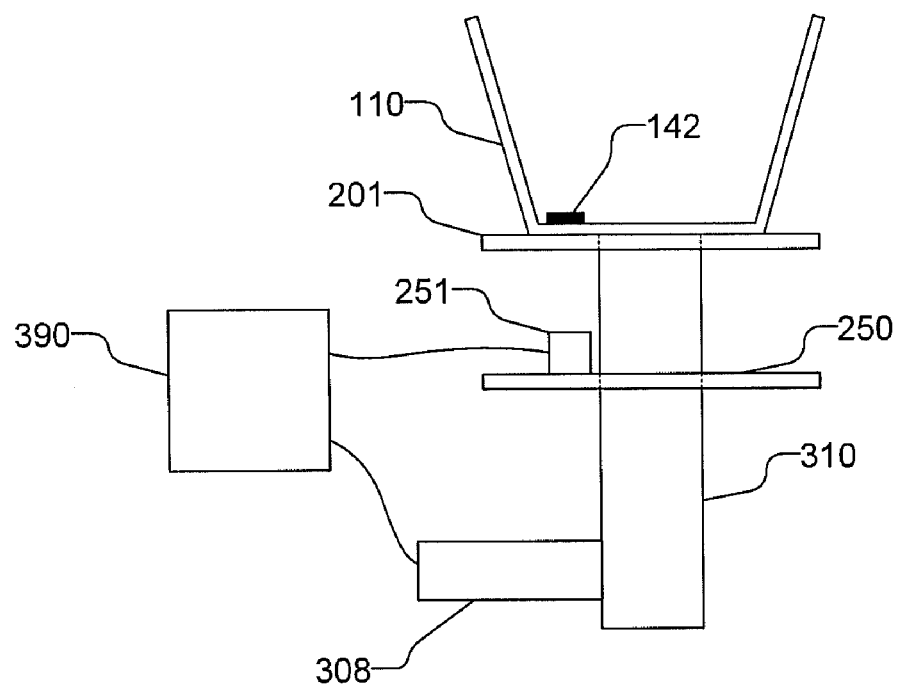
FIG. 16 schematically illustrates a gas feedback loop for one well.

The gas supply and sensors may be linked together in a feedback loop. FIG. 16 schematically illustrates a feedback loop for one well 110. As illustrated, in FIG. 16, a detection head on the optics plate 250 is coupled to a processor 390 that is also coupled to a solenoid 308. The pH level in the contents of the well 110, as measured by the sensor 142 and detection head, is determined by the processor 390. The processor 390 controls the solenoid 308 to provide the appropriate amount of gas to the well 110 to produce the desired pH level. The detection and control of the dissolved oxygen content is controlled in a similar manner.

Figure 17:
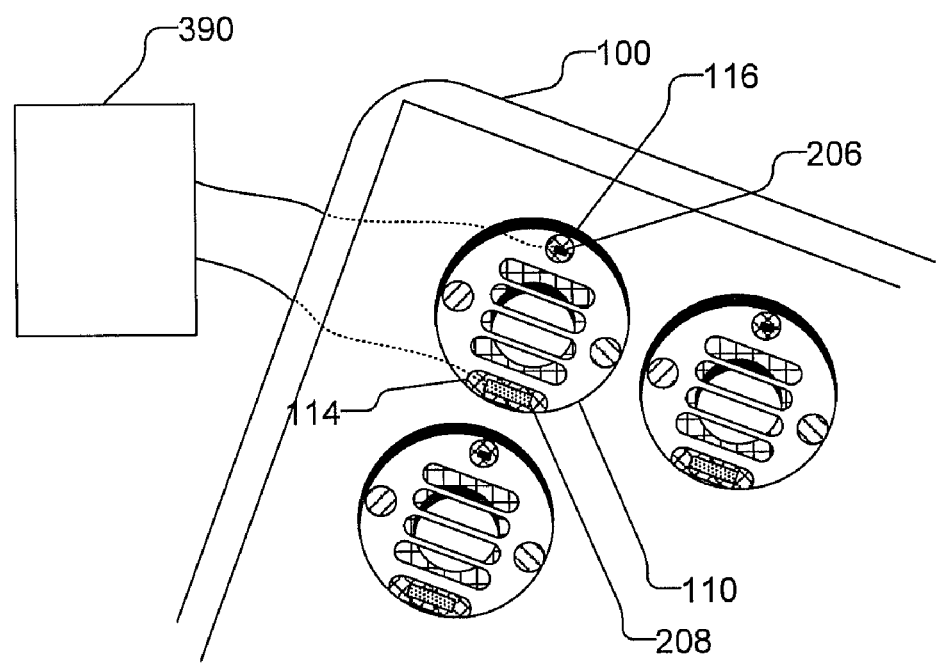
FIG. 17 illustrates top view of a portion of the well plate with a well over the support plate and a temperature feedback loop.

Additionally, the temperature of the contents of the well 110 is controlled in a feedback loop. FIG. 17 illustrates top view of a portion of the well plate 100 with a well 110 over the support plate 201. The membrane 130 is not shown so that the temperature control element 206 and temperature measurement element 208 can be seen through the apertures 114 and 116, respectively. As illustrated, the temperature control element 206 and temperature measurement element 208 are coupled to the processor 390. In order to control the temperature of the contents of a well, the processor 390 controls the temperature control element 206 based on the temperature measurement element 208 measurements. The temperature control elements 206 and temperature measurement element 208 for each well are individually coupled to the processor 390 so that the temperature in each individual well 110 can be independently controlled.

Figure 18:
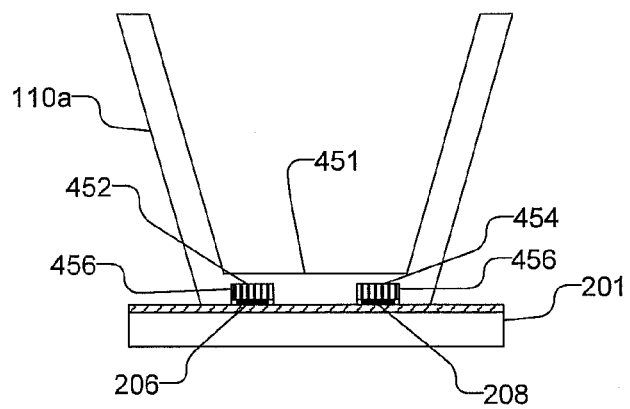
FIG. 18 illustrates a side view of a well with a temperature control element and temperature measurement element in thermal contact with the interior of the well.

It should be understood that the temperature control elements 206 and temperature measurement element 208 may be in thermal contact with the interior of the well 110 through a surface wall of the well. By way of example, FIG. 18 illustrates a side view of a well 110a along with a portion of the support plate 201 and temperature control element 206 and temperature measurement element 208 in thermal contact with the interior of the well 110a. The well 110a is similar to well 110 in FIGS. 2 and 3, but does not include apertures that extend through bottom surface for the temperature control and temperature measurement elements 206, 208. Well 110a includes indentations 452 and 454 in the exterior of the bottom surface 451. The indentations are at least partially filled with a thermally conductive material 456, such as a conductive silicon material. An adequate thermally conductive material is referred to as Gap Pad and may be purchased from Bergquist Co., located in Chanhassen Minn. The temperature control elements 206 and temperature measurement element 208 are in thermal contact with the interior of the well 110a through the thermally conductive material 456 and the bottom surface 451 of the well 110a. In some embodiments, the thermally conductive material 456 is not used and the temperature control elements 206 and temperature measurement element 208 are in thermal contact with the interior of the well 110a through the surface 451 of the well 110a.

Figure 19:
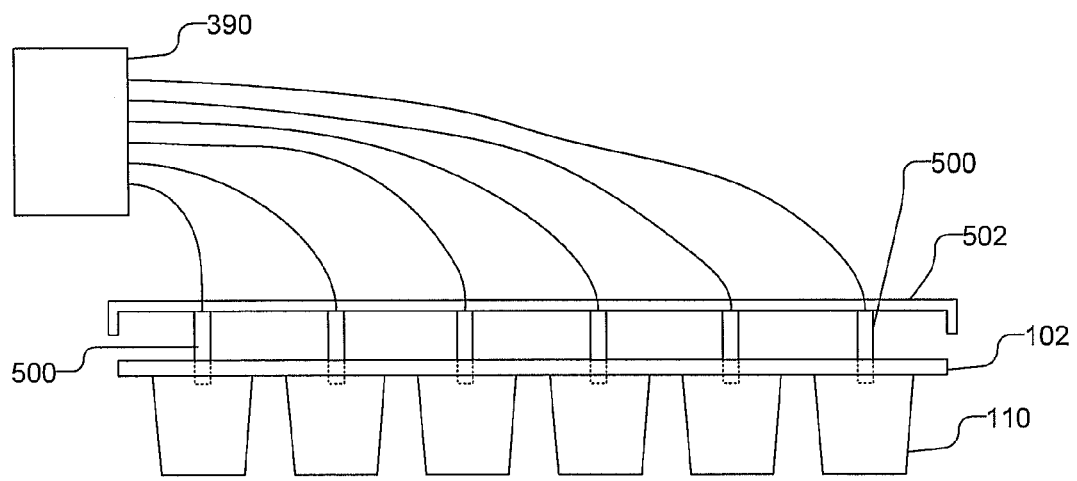
FIG. 19 illustrates an alternative embodiment for sensing the dissolved oxygen and/or pH level in the wells.

FIG. 19 illustrates an alternative embodiment for sensing the dissolved oxygen and/or pH level in the wells 110. As illustrated in FIG. 19, probes 500 can be physically inserted into the wells 110 in order to sense the dissolved oxygen and/or pH level. Probes 500 may, e.g., extend downward from the lid 502 of the well plate 100 and are inserted into the media in the wells 110 when the lid is placed on the well plate 100. The probes 500 are connected to the processor 390 when the well plate 100 and lid 502 are placed in the device 150.

In one embodiment, probes 500 can be used for oxygen sensing. By way of example, an oxygen sensing probe may be a polarographic (Ross or Clark Cell) and galvanic cell probes. Manufactures of probes that may be used for this purpose include Diamond General and Broadley James. A polarographic or galvanic probe 500 may be also be used with the well from the bottom, where the electrolytes and electrodes of the polarographic or galvanic probe 500 is separated from the media in the well 100 by the membrane 130. In such an embodiment, an additional aperture in the well 110 would be necessary for each probe. Alternatively, probes 500 may be an optical fiber with a fluorescent material attached to the end of the fiber. The approach is similar to the sensors 140 and 142 discussed above, but the sensor is attached directly to the fiber. A manufacturer of an optical fiber probe that may be used is Ocean Optics.

Where the probes 500 are used to sense the pH level in the media contained in the wells 110, the probe may be a "glass electrode". Glass electrodes are manufactured from a glass that has an electrostatic potential that is dependent on the environmental pH. Alternatively, the probe 500 may include an ion-sensitive FET (ISFET), which is sensitive to the environmental pH. A manufacturer of an ISFET that may be used is Sentron. In another embodiment, the probe 500 may be a transmission probe that uses a pH dye on an embedded film. Light is passed through the film with the dye and the transmission is measured, which indicates the pH level. Ocean Optics manufactures transmission probes that may be used. The light source for the transmission probe may be either an LED or a white light source, such as a flash lamp. A photodiode is used to detect the light. The measurement may be made at two wavelengths. The ratio of the two wavelengths provides information as to the pH level. In order to perform two measurements at different wavelengths, either two light sources, two detectors (each with a filter), or a spectrometer is needed.

If desired, different types of sensors may be used to measure the dissolved oxygen and pH level. Thus, for example, the dissolved oxygen may be measured using sensor 140 while the pH is measured with probe 500. Alternatively, both the dissolved oxygen and pH level may be measured using probes.

Additional measurement devices may be used with the present invention. For example, it may be desirable to measure cell density, e.g., using optical density and/or impedance. Further, it may be desirable to measure the concentration of fluorescently tagged protein or substrate during fermentation.

Figure 20:
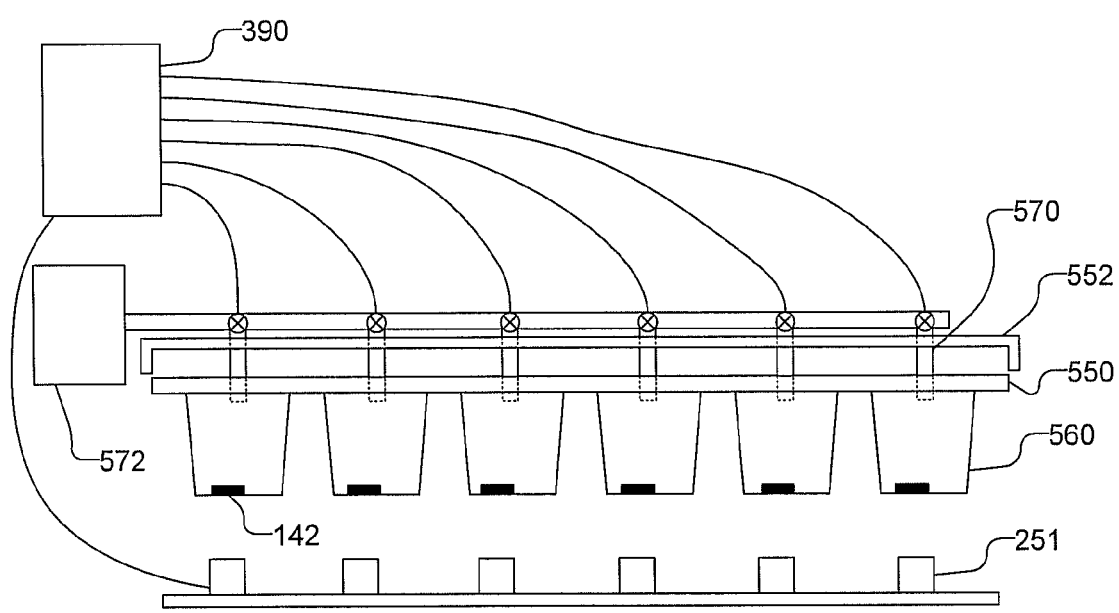
FIG. 20 illustrates an embodiment in which a drip valve is used with the well plate.

In another embodiment, the pH level is controlled using a liquid drip valve instead of a gas supply. FIG. 20 illustrates a side view of a well plate 550, which is similar to well plate 100, except that the wells 560 do not include a gas supply aperture in the bottom surface. As illustrated in FIG. 20, a series of drip valves 570 are positioned relative to the well plate 550 such that at least one drive valve 570 is held over the wells 560. The drip valves 570 may extend and/or may be held by the lid 552 of the well plate 550. The drip valves 570 are coupled to a supply 572, which provides the desired liquid to the drip valves 570 to adjust the pH level in the contents of the well 560, such as dilute NaOH or acid. The drip valves are coupled to and controlled by the processor 390. The detection heads 251 associated with each well 560 provide information to the processor 390 regarding the pH level of individual wells. In response the processor 390 controls the flow of liquid into the wells 570 to adjust the pH level to the desired level. The drip valves 570 may be, e.g., peristaltic or syringe pumps or a micro valve. If control over the dissolved oxygen is desired, a gas supply may be provided to the well, e.g., through an aperture in the bottom of the well, as described above.

Although the present invention is illustrated in connection with specific embodiments for instructional purposes, the present invention is not limited thereto. Various adaptations and modifications may be made without departing from the scope of the invention. Therefore, the spirit and scope of the appended claims should not be limited to the foregoing description.

What is claimed is:

1. An apparatus including a well plate that has a plurality of wells, each well being defined by at least one surface that defines an interior cavity having an opening, the apparatus comprising: a plurality of drip valves and the well plate, wherein there is at least one drip valve associated with each well positioned over the opening of each well, wherein each well comprises: at least one aperture through the at least one surface of the well, the aperture configured to provide a gas supply access to the interior of the well, wherein the at least one aperture through the at least one surface of the well is different than the opening of the cavity that is defined by the at least one surface; and at least one of a pH level sensor and a dissolved oxygen sensor disposed within the well, the drip valves configured to provide a liquid to the interior cavities of the associated wells; a plurality of detectors for detecting a property of the contents of the wells, wherein there is at least one detector associated with each well; and a control system coupled to the plurality of detectors and the plurality of drip valves, the control system controlling the amount of the liquid provided by the drip valves to the associated wells in response to the property of the contents in the associated wells detected by the detectors associated with each well.

2. The apparatus of claim 1, wherein the liquid is an aqueous solution comprising one of NaOH and acid.

3. The apparatus of claim 1, further comprising a gas supply for providing gas to the interior cavities of the associated wells, wherein the control system is coupled to the gas supply, the control system controlling the amount of gas provided by the gas supply to the associated wells in response to the property of the contents in the associated wells detected by the detectors associated with each well.

4. The apparatus of claim 1, wherein the at least one of a pH sensor and a dissolved oxygen sensor disposed within each well in the well plate includes at least one fluorescent material disposed within the well, the at least one fluorescent material reacts to the property of the contents of the well, wherein the plurality of detectors comprise:
at least one light source configured to illuminate the fluorescent material; and
at least one photodetector for detecting the light emitted by the fluorescent material.

5. The apparatus of claim 1, wherein the light source illuminates the fluorescent material at a frequency and wherein detector measures the phase delay of the light emitted by the fluorescent material.

6. The apparatus of claim 1, wherein the plurality of detectors comprises at least one probe that extends into the interior cavity of the well.

7. The apparatus of claim 4, wherein each well is defined by a bottom surface and at least one side surface and wherein the at least one of a pH level sensor and a dissolved oxygen sensor are disposed on the interior of the bottom surface of the well.

8. The apparatus of claim 1, wherein the at least one of a pH level sensor and a dissolved oxygen sensor comprise at least one probe that is coupled to the interior of the well.

9. The apparatus of claim 8, further comprising a lid configured to be placed over the plurality of wells, wherein the at least one probe extends from the lid into the interior of the well.

10. The apparatus of claim 1, further comprising at least one membrane coupled to the at least one surface of each well and covering the at least one aperture, wherein the membrane is formed from a gas permeable material and the gas is supplied through the membrane.

11. The apparatus of claim 1, wherein each well comprises a plurality of apertures through the at least one surface of the well, the plurality of apertures configured to provide a gas supply access to the interior of the well.

12. The apparatus of claim 1, wherein each well further comprises: a second aperture through the at least one surface of the well, the second aperture configured to place a temperature control element in thermal contact with the interior of the well; and a third aperture through the at least one surface of the well, the third aperture configured to place a temperature measurement element in thermal contact with the interior of the well.

13. The apparatus of claim 1, wherein each well has a bottom and the at least one aperture is through the bottom.

14. The apparatus of claim 3, further comprising: at least one gasket for providing a seal with at least one well in the well plate, the gasket having at least one aperture associated with each well, wherein the gas supply provides gas through the aperture in the gasket.

* * * * *